United States Patent [19]

van Andel

[11] Patent Number: Plant 6,197

[45] Date of Patent: Jun. 7, 1988

[54] ALSTROEMERIA VARIETY 'STAPIRAM'

[75] Inventor: Jacob van Andel, Aalsmeer, Netherlands

[73] Assignee: Van Staaveren B.V., Aalsmeer, Netherlands

[21] Appl. No.: 872,870

[22] Filed: Jun. 11, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; W. Dennis Drehkoff

[57] ABSTRACT

A new hybrid Alstroemeria plant characterized by its very large flowers which have an overall red-purple coloration of its petals which is sharply offset by the bright yellow coloration in the lower body portion of the inside petals each of which is marked with short pencil stripes extending outwardly from the base of the inner petal to all of its margins except its apex portion; this plant being furthered distinguished by its strong, vigorous, upright growth with the main stems reaching a height of about 2.5 meters and the flowers being produced profusely and continuously the year around.

1 Drawing Sheet

BACKGROUND OF THE NEW PLANT

This hybrid Alstroemeria originated as a seedling resulting from my crossing of plants selected from my breeding stock maintained at Aalsmeer, The Netherlands, for breeding purposes, the selected plants being individually identified in the breeding records maintained at my office at Aalsmeer. The object of this crossing was to develop a plant having year-round flower production with a new color and this particular seedling was selected by me for propagation and test because it appeared to satisfy my objective purposes and this selected plant was asexually reproduced by division of its rhizomes with very satisfactory results, which prompted me to direct that continued propagation be carried on through several successive generations by dividing the rhizomes of the respective generations, which demonstrated to my satisfaction that this new plant would maintain its distinctive characteristics from generation to generation and that those characteristics were firmly fixed.

DESCRIPTION OF THE DRAWING

This new Alstroemeria variety is illustrated by the accompanying photographic drawing which shows a group of the flowers of a blooming plant in full color, the view demonstrating the unique and distinctive coloration and form of the flowers, the color rendition being as nearly true as it is possible to obtain by conventional photographic procedures.

DESCRIPTION OF THE NEW PLANT

The following is a detailed description of my new Alstroemeria variety as observed at Aalsmeer, The Netherlands, with color designations according to The R.H.S. Colour Chart of The Royal Horticultural Society of London, England.

THE PLANT

Origin: Seedling.

Parentage:

*Seed parent.*—Breeding Stock Plant No. Aur. or 7.

*Pollen parent.*—Breeding Stock Plant No. 0384-15. These stock plants are unnamed and unpatented and the identification of each is recorded in my breeding records maintained at my office at Aalsmeer.

Classification: Alstroemeria hybrid.

Form: Erect and very tall bush.

Height: Up to about 2.5 meters.

Growth: Vigorous, strong and upright.

Growth Rate: Fast.

Foliage: Abundant.

*Number of Leaves.*—Varying with season.

*Size of Leaf.*—Large.

*Leaf shape.*—Elliptic with entire and slightly curved margins.

*Texture.*—Smooth.

*Color.*—Upper side — Middle Green. Under side — Grey Green.

Rhizomes:

*Color.*—White.

*Size.*—Varies with age of plant.

THE BUD

Form: Pear shaped.

Size: Normal.

*Diameter.*—About 2 cm.

*Length.*—About 3.5 cm.

Calyx: This plant has no calyx, the six petals of the flower being perianth and dividing simultaneously.

Peduncle:

*Length.*—About 10 to 12 cm.

*Character.*—Strong and erect.

*Color.*—Medium Green.

THE FLOWER

Blooming habit: Continuous and profusely the year around.

Flower size: Very large.

*Diameter.*—About 6.5 to 7 cm.

*Depth.*—About 6 cm.

Borne: Singly.

Shape: Cup-shaped with petal tips curving slightly outward.

Petalage:

*Number of Petals.*—Six.

*Arrangement.*—Two concentric circles of three petals each.

*Form.*—Obovate with emarginate apex.
*Texture.*—Soft.
*Appearance.*—Satiny.
*Color.*—Outer petals: Top and reverse sides, 59D, with some shading of 59B-C on the inner body parts. Inside petals: Lower midbody portion, 12A. Outer portion and base, 59B-C. Reverse side, 59D and 10A.

Peduncle:
*Length.*—1 cm.
*Color.*—Green.

Fragrance: None.

Persistence: The flowers hang on and dry.

Lasting quality:
*On the plant.*—About 14 days.
*As a cut flower.*—About 10 days.

REPRODUCTIVE ORGANS

Stamens:
*Number.*—Six.
*Arrangement.*—Normal.

Anthers:
*Size.*—About 10 mm.

*Color.*—Violet.

Filaments:
*Length.*—About 6 to 6.5 cm.
*Color.*—Pink.

Pollen:
*Color.*—Grey green.

Pistils:
*Number.*—One.

Style:
*Length.*—About 3.5 cm.
*Color.*—Pink.

Stigma:
*Color.*—Pink.

I claim:

1. A new and distinctive Alstroemeria hybrid, substantially as herein shown and described, characterized by its fast growth to a very tall height with a continuous and profuse production of flowers having generally an overall red-purple coloration, with the exception of the inner petals which have a midportion near the base of a bright yellow color.

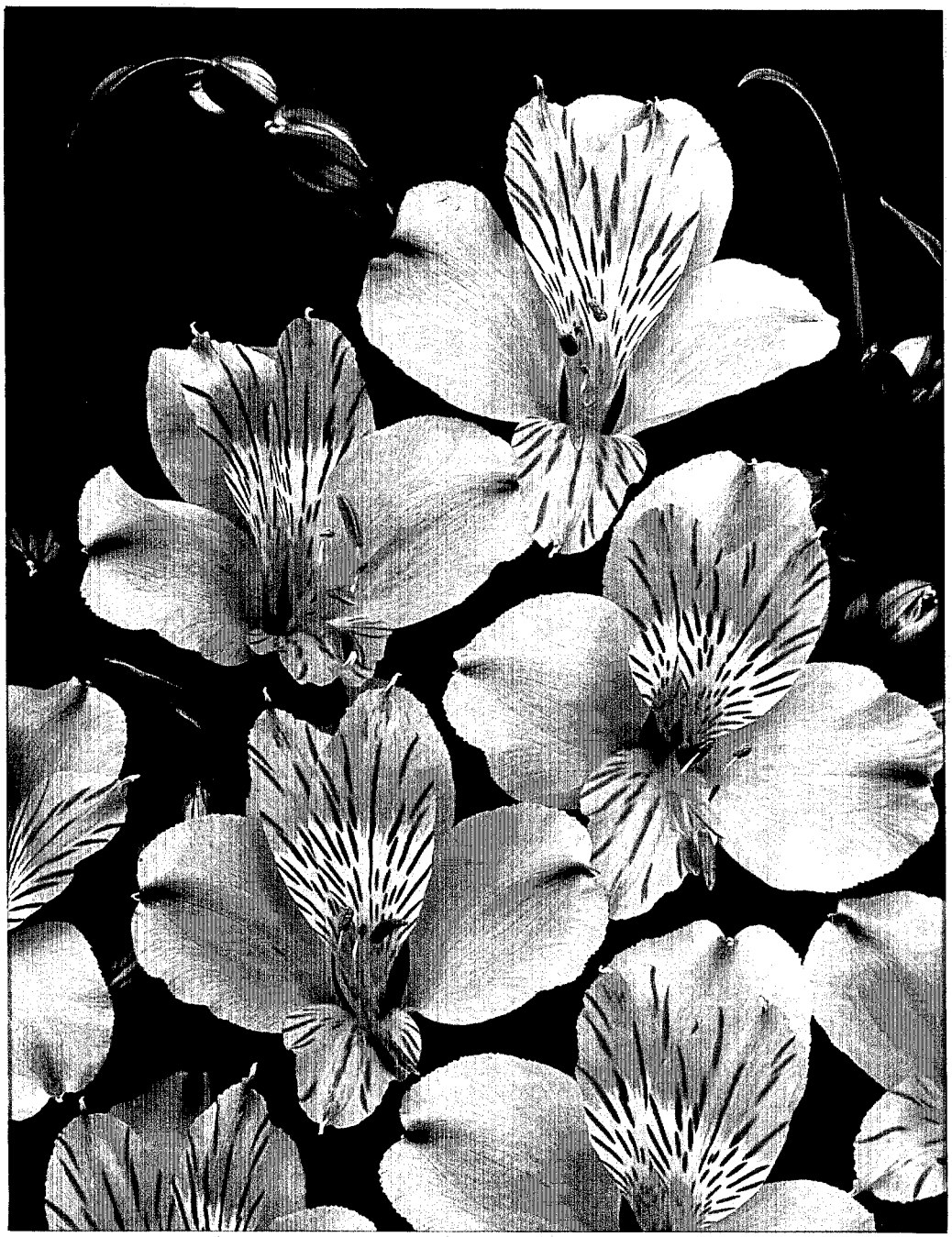

* * * * *